(12) United States Patent
Kakinuma

(10) Patent No.: US 11,666,718 B2
(45) Date of Patent: Jun. 6, 2023

(54) RESPIRATORY INFORMATION ACQUISITION DEVICE AND RESPIRATORY INFORMATION ACQUISITION METHOD

(71) Applicant: Teijin Pharma Limited, Tokyo (JP)

(72) Inventor: Eisuke Kakinuma, Tokyo (JP)

(73) Assignee: Teijin Pharma Limited, Tokyo (JP)

( * ) Notice: Subject to any disclaimer, the term of this patent is extended or adjusted under 35 U.S.C. 154(b) by 484 days.

(21) Appl. No.: 16/497,147

(22) PCT Filed: Mar. 12, 2018

(86) PCT No.: PCT/JP2018/009378
§ 371 (c)(1),
(2) Date: Sep. 24, 2019

(87) PCT Pub. No.: WO2018/180392
PCT Pub. Date: Oct. 4, 2018

(65) Prior Publication Data
US 2020/0016351 A1    Jan. 16, 2020

(30) Foreign Application Priority Data

Mar. 31, 2017 (JP) .............................. JP2017-071190

(51) Int. Cl.
  *A61M 16/00* (2006.01)
  *A61M 16/10* (2006.01)
  *A61M 16/06* (2006.01)

(52) U.S. Cl.
CPC ........ *A61M 16/024* (2017.08); *A61M 16/101* (2014.02); *A61M 16/0672* (2014.02);
(Continued)

(58) Field of Classification Search
CPC .............. A61M 16/024; A61M 16/101; A61M 2016/0027; A61M 16/0672;
(Continued)

(56) References Cited

U.S. PATENT DOCUMENTS

| 2004/0134496 A1* | 7/2004 | Cho ..................... A61B 5/0816 |
| | | 128/204.23 |
| 2005/0121033 A1* | 6/2005 | Starr ..................... A61M 16/06 |
| | | 128/204.23 |

(Continued)

FOREIGN PATENT DOCUMENTS

| CN | 1893995 A | 1/2007 |
| CN | 101843489 A | 9/2010 |

(Continued)

OTHER PUBLICATIONS

International Search Report for PCT/JP2018/009378 dated Jun. 5, 2018 (PCT/ISA/210).

(Continued)

*Primary Examiner* — Samchuan C Yao
*Assistant Examiner* — Tyler A Raubenstraw
(74) *Attorney, Agent, or Firm* — Sughrue Mion, PLLC

(57) ABSTRACT

A respiratory information acquisition device used for a PSA type oxygen concentration device that switches and uses multiple adsorption cylinders includes a respiratory information acquisition means of measuring a first pressure of a periodic pressure fluctuation in an oxygen supply path when oxygen is supplied to a patient from the PSA type oxygen concentration device and a second pressure of a periodic pressure fluctuation in the oxygen supply path when oxygen is not supplied to the patient from the PSA type oxygen concentration device, a phase confirmation means of matching phases of the first pressure and the second pressure, and a subtraction processing means of calculating a difference between the first pressure and the second pressure in the condition where the phases are matched.

7 Claims, 4 Drawing Sheets

(52) U.S. Cl.
CPC ............... *A61M 2016/0027* (2013.01); *A61M 2202/0208* (2013.01)

(58) Field of Classification Search
CPC .......... A61M 2202/0208; A61M 16/00; A61M 2016/0015; A61M 2016/018; A61M 2016/0033; A61M 2016/003; A61M 16/0021; A61M 2205/3331; A61M 2205/3334; A61M 2205/52; A62B 7/02; A61B 5/7217; A61B 5/08; A61B 5/0816; A61B 5/0826; A61B 5/087; A61B 5/4812; A61B 5/4806; G01R 23/00
See application file for complete search history.

(56) References Cited

U.S. PATENT DOCUMENTS

| | | | | |
|---|---|---|---|---|
| 2008/0110461 | A1* | 5/2008 | Mulqueeny | A61M 16/0051 128/204.23 |
| 2008/0302364 | A1* | 12/2008 | Garde | A61M 16/201 128/204.23 |
| 2009/0050154 | A1* | 2/2009 | Strothmann | A61M 16/161 128/204.23 |
| 2010/0249611 | A1 | 9/2010 | Chen et al. | |
| 2010/0252042 | A1* | 10/2010 | Kapust | A61M 16/0883 128/204.23 |
| 2010/0300444 | A1* | 12/2010 | Decker | A61M 16/024 381/71.7 |
| 2011/0034819 | A1 | 2/2011 | Desforges et al. | |
| 2012/0125337 | A1* | 5/2012 | Asanoi | A61M 16/101 128/204.23 |
| 2012/0157857 | A1 | 6/2012 | Abe et al. | |
| 2012/0203128 | A1* | 8/2012 | Levison | A61B 5/6819 600/537 |
| 2013/0167842 | A1 | 7/2013 | Jafari et al. | |
| 2014/0007870 | A1* | 1/2014 | Franberg | A61M 16/208 128/204.23 |
| 2014/0137859 | A1* | 5/2014 | Wilkinson | A61M 16/0816 128/202.26 |
| 2014/0216453 | A1* | 8/2014 | Whitcher | A61M 16/10 128/202.26 |
| 2015/0059764 | A1 | 3/2015 | Metelits | |
| 2015/0196245 | A1* | 7/2015 | Peake | A61B 5/18 128/202.13 |
| 2016/0045695 | A1* | 2/2016 | Kapust | A61M 16/0003 128/204.23 |
| 2016/0166796 | A1* | 6/2016 | Orr | A61M 16/201 128/202.22 |
| 2016/0338650 | A1* | 11/2016 | Wang | A61B 5/7217 |
| 2017/0281897 | A1* | 10/2017 | Vink | A61M 16/204 |
| 2017/0340851 | A1* | 11/2017 | Allum | A61M 16/0672 |
| 2018/0117270 | A1* | 5/2018 | Bassin | A61M 16/16 |
| 2018/0132744 | A1* | 5/2018 | Yu | A61B 5/7275 |
| 2018/0140252 | A1* | 5/2018 | Luxon | A61B 5/6826 |
| 2018/0280646 | A1* | 10/2018 | Freeman | A61M 16/0003 |

FOREIGN PATENT DOCUMENTS

| | | | | |
|---|---|---|---|---|
| CN | 102551726 A | | 7/2012 | |
| EP | 1 850 917 | | 11/2007 | |
| JP | 06-190045 A | | 7/1994 | |
| JP | 07-096035 A | | 4/1995 | |
| JP | 2001-286566 A | | 10/2001 | |
| JP | 2002-241110 A | | 8/2002 | |
| JP | 2011-518016 A | | 6/2011 | |
| JP | 2012-183158 A | | 9/2012 | |
| JP | 2012-183159 A | | 9/2012 | |
| JP | 2015-085191 A | | 5/2015 | |
| JP | 2016-536081 A | | 11/2016 | |
| WO | WO-2006005432 A1 * | | 1/2006 | ........ A61M 16/0051 |
| WO | 2006/086416 A2 | | 8/2006 | |
| WO | WO-2008048950 A2 * | | 4/2008 | ........ A61M 16/0051 |
| WO | 2010/097717 A1 | | 9/2010 | |
| WO | 2012/162389 A1 | | 11/2012 | |
| WO | WO-2013173219 A1 * | | 11/2013 | ............ A61B 5/087 |
| WO | WO-2015105787 A1 * | | 7/2015 | ......... A61B 5/02055 |
| WO | WO-2016145483 A1 * | | 9/2016 | ........... A61B 5/0826 |

OTHER PUBLICATIONS

Extended European Search Report, dated Dec. 9, 2020, issued by the European Patent Office in European Patent Application No. 18776487.3.

\* cited by examiner

[Fig. 1]
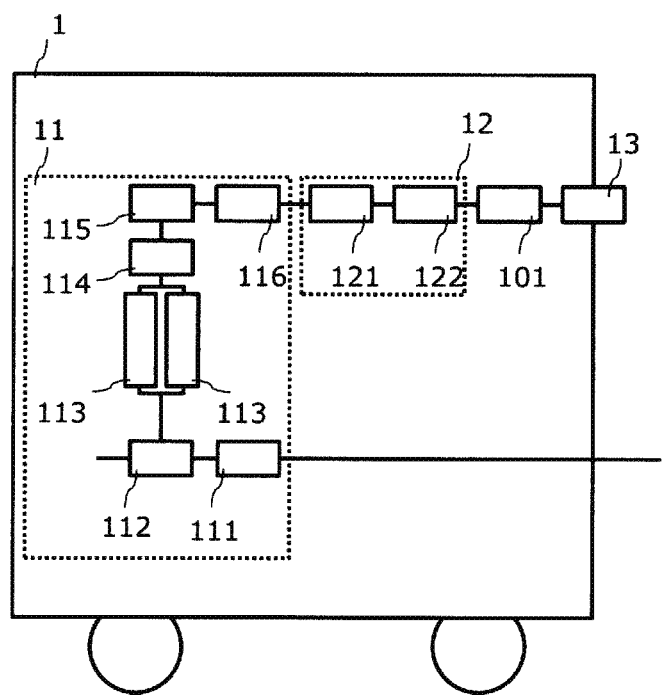
[Fig. 2]
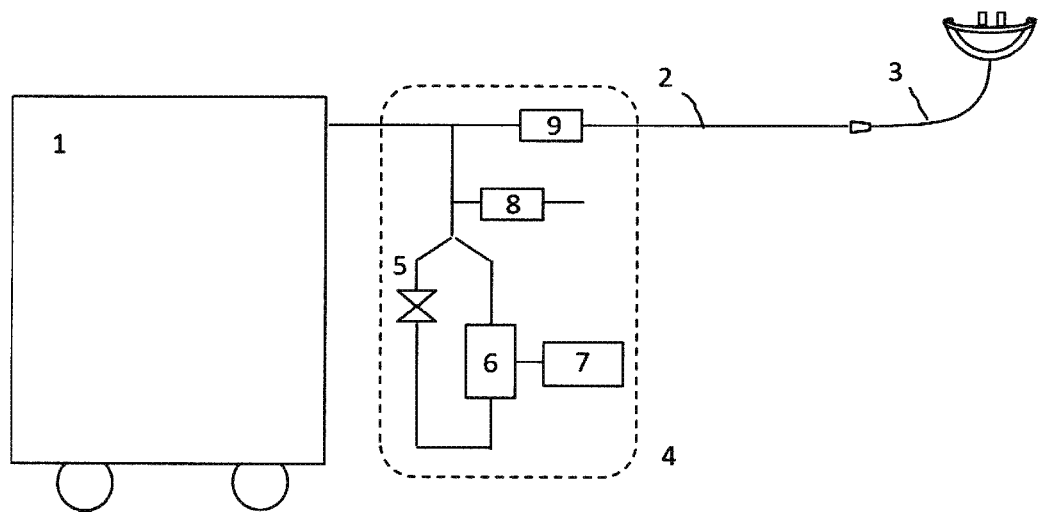

[Fig. 3]
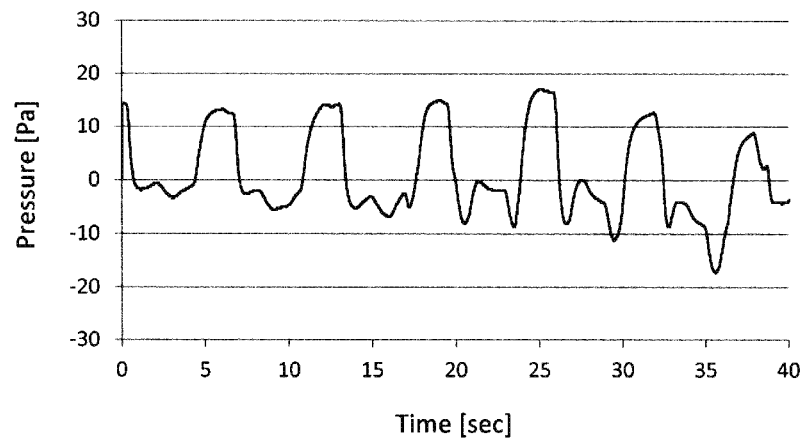
[Fig. 4]
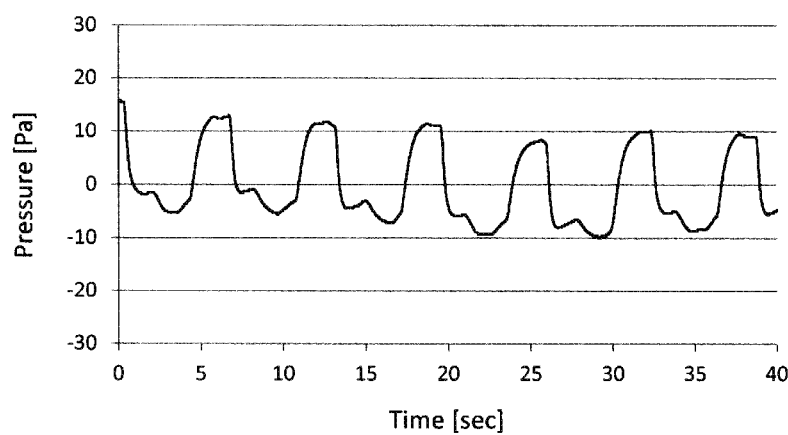
[Fig. 5]
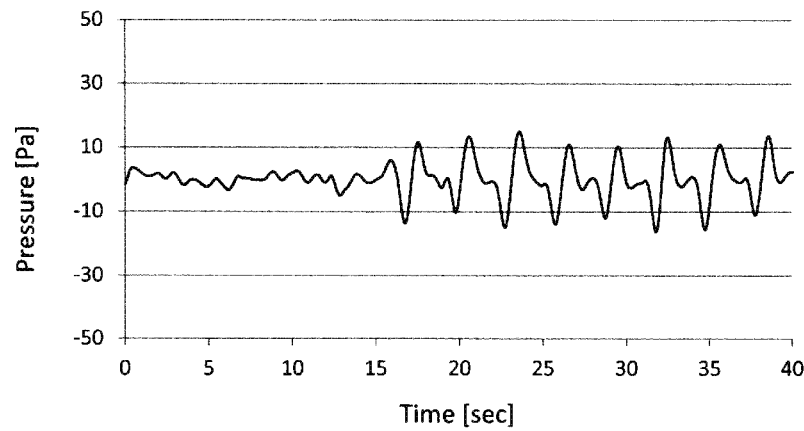

[Fig. 6]
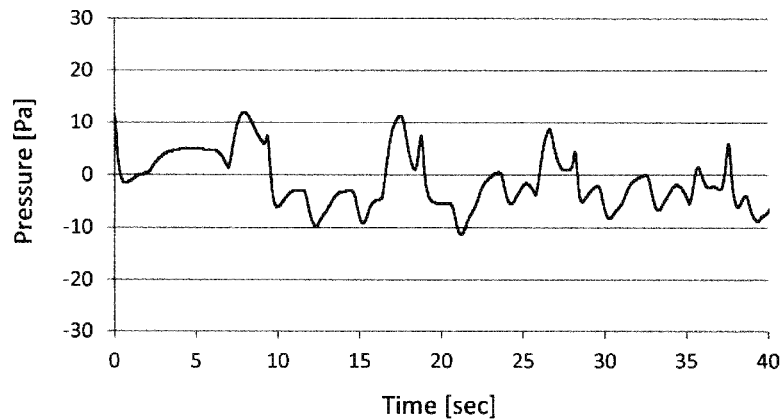
[Fig. 7]
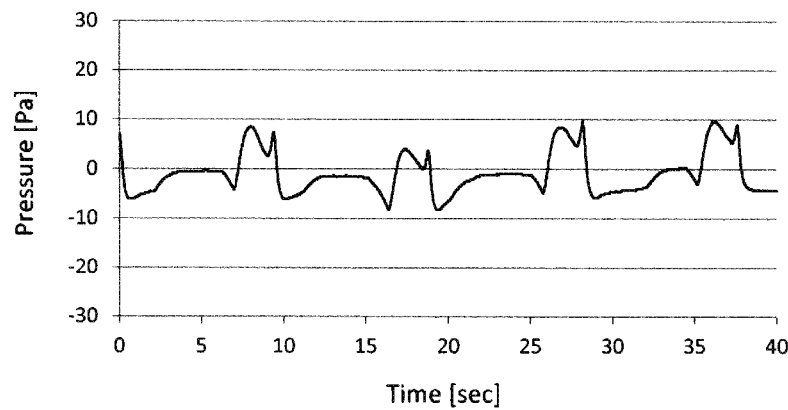
[Fig. 8]
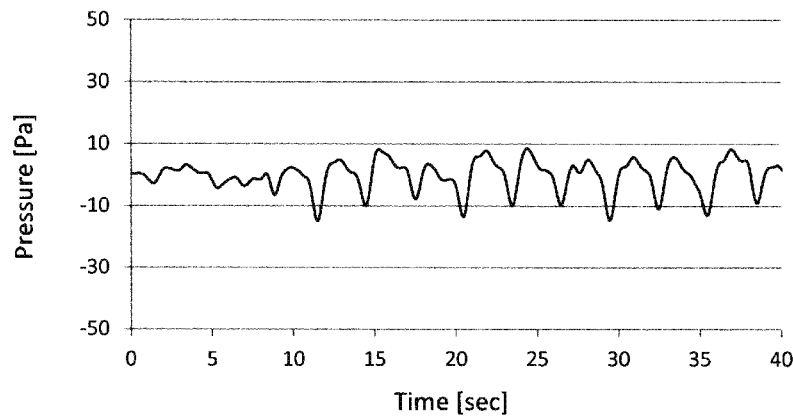

[Fig. 9]
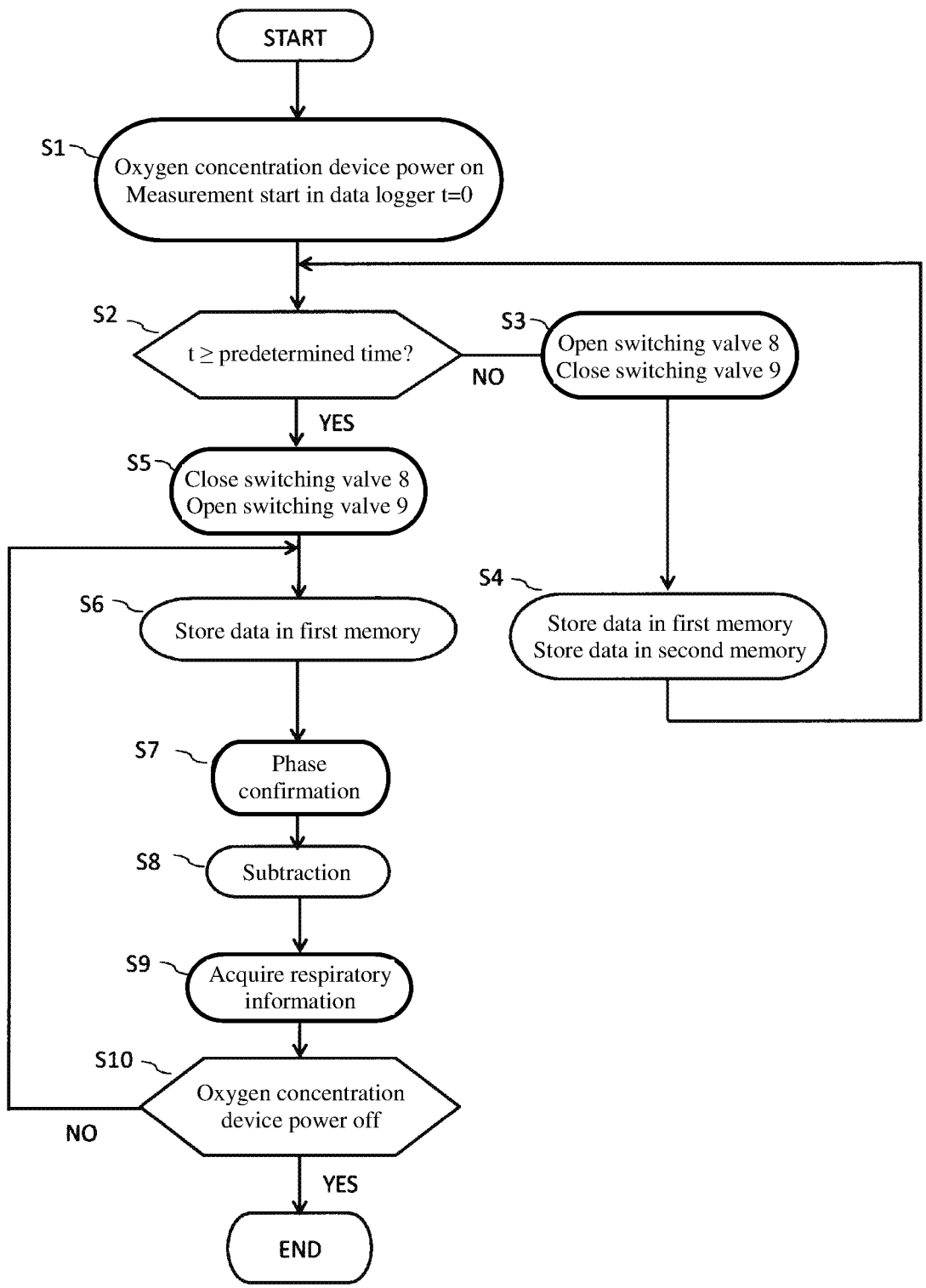

RESPIRATORY INFORMATION ACQUISITION DEVICE AND RESPIRATORY INFORMATION ACQUISITION METHOD

CROSS REFERENCE TO RELATED APPLICATIONS

This application is a National Stage of International Application No. PCT/JP2018/009378 filed Mar. 12, 2018, claiming priority based on Japanese Patent Application No. 2017-071190 filed Mar. 31, 2017.

TECHNICAL FIELD

The present invention relates to a respiratory information acquisition device and a respiratory information acquisition method used for a PSA type oxygen concentration device.

BACKGROUND ART

Conventionally, an oxygen therapy is provided as one treatment for patients with respiratory diseases such as asthma, chronic obstructive pulmonary disease and the like. This is a therapy to make the patients inhale oxygen gas or an oxygen-enriched gas. In recent years, a home oxygen therapy (HOT) to inhale oxygen at home, a facility or the like for the purpose of improving QOL of patients has become mainstream, and the therapy mainly uses an oxygen concentration device for an oxygen supply.

The oxygen concentration device is a device for concentrating oxygen, which occupies about 21% of air, and discharging the concentrated gas. Many of the oxygen concentration devices commonly adopt a Pressure Swing Adsorption type (hereinafter, PSA type, and PSA type oxygen concentration device is simply referred to as oxygen concentration device).

In the PSA type oxygen concentration device, air is taken into a cylinder filled with an adsorbent selectively adsorbing nitrogen gas, and concentrated oxygen gas is generated by repeating compression and decompression. Using this mechanism, the oxygen concentration device can provide high concentration oxygen gas to the patients continuously.

The main disease of the patients receiving a home oxygen therapy is chronic obstructive pulmonary disease (hereinafter, COPD). COPD is an irreversible disease with symptoms of cough/sputum and exertional dyspnea caused by bronchial stenosis or break of alveolar wall.

The symptom of COPD may worsen to breathlessness and an increase in respiratory rate and even to "the condition requiring a change of/addition to the treatment for a stable phase" called an acute exacerbation of COPD. An acute exacerbation of COPD often requires hospitalization, and may cause a risk of respiratory failure and even a crisis of life. In addition, even if the patient can leave the hospital, it is not unusual for the patient to have a symptom of a stable phase worse than before hospitalization and to repeat hospitalization and release.

Thus, it is very important to take an early treatment before the symptom worsens to require hospitalization by an acute exacerbation of COPD, and for this purpose, the respiratory information of the patient in home oxygen therapy is a very useful information source for grasping the clinical conditions of the patient.

At the same time, it is also very important for the patient to inhale the concentrated oxygen gas according to the flow rate prescribed by the physician after diagnosis. However, the correct inhalation of oxygen is disturbed by a slip-off of a cannula during sleep, a come-off of a tube during work, and the like, and the patient may take off cannula intentionally for some reason even when the oxygen concentration device is running. Any situation where the patient cannot inhale the oxygen in spite of the oxygen concentration device being run has a risk of exacerbating the clinical conditions of the patient.

Therefore, the acquisition of the respiratory information of the patient inside the oxygen concentrator during the operation of the oxygen concentration device enables confirmation of the actual use conditions of the patient such as connection between the oxygen concentration device and the patient via the oxygen supply tube as well as acquisition of the respiratory information of the patient at the same usability as common conventional oxygen concentration devices, thereby realizing very useful means.

CITATION LIST

Patent Literature

[PTL 1] Japanese Unexamined Patent Application Publication No. H06-190045
[PTL 2] Japanese Unexamined Patent Application Publication No. 2001-286566
[PTL 3] Japanese Unexamined Patent Application Publication No. H07-96035
[PTL 4] Japanese Unexamined Patent Application Publication No. 2015-85191
[PTL 5] Japanese Unexamined Patent Application Publication (Translation of PCT Application) No. 2011-518016

SUMMARY OF INVENTION

Technical Problem

The method to acquire the respiratory information of the patient during the operation of an oxygen concentration device includes a method of equipping a fine differential pressure sensor for respirometry between the oxygen concentration device and the cannula attached to the patient and measuring the respiratory pressure of the patient during oxygen inhalation as disclosed in PTL 1 and 2. However, as a result of diligent examination of the inventors of the present application, it has been revealed that pressure fluctuation applied to the differential pressure measurement system includes pressure fluctuation caused by compression/decompression during generation of the concentrated oxygen gas. The oxygen concentration device adopts a PSA type operation method as mentioned above, which makes also the flow rate of the supply oxygen fluctuate, and thus the pressure fluctuation due to PSA always appears in the oxygen supply path. For this reason, in the environment where the respiratory pressure of the patient is measured simply using a fine differential pressure sensor, the respiratory pressure of the patient is detected including the pressure fluctuation due to PSA, and thus the respiratory information of the patient cannot be acquired with good accuracy. Especially in the case of adding an extension tube or setting the flow rate range to 3.0 L/m or larger, the acquisition of the respiratory information of the patient becomes impossible.

Besides, PTL 3 and 4 disclose a method of acquiring the respiratory information of the patient, wherein the respiratory pressure of the patient during oxygen inhalation is measured using a fine differential pressure sensor, and then the respiratory pressure data obtained are processed by software. However, the method in prior art cannot acquire respiratory information of the patient with good accuracy, since the method does not consider the pressure fluctuation due to PSA which is superimposed on the respiratory pressure of the patient.

On the other hand, PTL 5 discloses a method of acquiring the respiratory information from the respiratory pressure data obtained using a frequency analysis. However, the frequency analysis has a difficulty in separating the respiration component from the pressure swing component due to PSA, and thus the method has a weak point of poor accuracy.

From the above consideration, in order to acquire the respiratory information of the patient during the operation of the oxygen concentration device, it is necessary to separate the respiration component from the pressure swing component due to PSA in the measured data of respiratory pressure of the patient.

Solution to Problem

The inventors of the present invention studied diligently to solve the above-mentioned problems so far in the method of acquiring the respiratory information of the patient during the operation of the oxygen concentration device, and arrived at the present invention.

That is, the present invention is a respiratory information acquisition device used for a PSA type oxygen concentration device that switches and uses multiple adsorption cylinders comprising: a respiratory information acquisition means of measuring a first pressure of a periodic pressure fluctuation in an oxygen supply path when oxygen is supplied to a patient from the PSA type oxygen concentration device and a second pressure of a periodic pressure fluctuation in the oxygen supply path when oxygen is not supplied to the patient from the PSA type oxygen concentration device, a phase confirmation means of matching phases of the first pressure and the second pressure, and a subtraction processing means of calculating a difference between the first pressure and the second pressure under the condition where the phases are matched.

The phase confirmation means may be a means of calculating data for one cycle of the pressure fluctuation of the first pressure and data for one cycle of the pressure fluctuation of the second pressure, and matching phases.

The phase confirmation means may be a means of detecting a peak pressure for each of the first pressure and the second pressure, and matching phases at the peak pressure.

The oxygen supply path may be equipped with a switching valve for allowing or shutting the oxygen supply from the PSA type oxygen concentration device to the patient.

The respiratory information acquisition means may be equipped with a fine differential pressure sensor and may measure a differential pressure between both ends of any point in the oxygen supply path and a point of constant pressure.

The present invention is a respiratory information acquisition method comprising: a respiratory information acquisition step of measuring a first pressure of a periodic pressure fluctuation in an oxygen supply path when oxygen is supplied to a patient from a PSA type oxygen concentration device that switches and uses multiple adsorption cylinders and a second pressure of a periodic pressure fluctuation in the oxygen supply path when oxygen is not supplied to the patient from the PSA type oxygen concentration device, a phase confirmation step of matching phases of the first pressure and the second pressure, and a subtraction step of calculating a difference between the first pressure and the second pressure under the condition where the phases are matched.

Advantageous Effects of Invention

In accordance with the present invention, respiratory information of a patient can be acquired by separating a respiration component of the patient from a pressure fluctuation component due to PSA while an oxygen concentration device is running.

BRIEF DESCRIPTION OF DRAWINGS

FIG. 1 illustrates a diagram of the configuration of the oxygen concentration device concerning embodiment 1.

FIG. 2 illustrates a diagram of the configuration for acquiring the respiratory information of a patient concerning embodiment 1.

FIG. 3 is a graph showing pressure data including the respiratory information of the patient under the condition of a continuous flow of 1 LPM and addition of a 10-m extension tube.

FIG. 4 is a graph showing PSA pressure data recorded beforehand under the condition of a continuous flow of 1 LPM and addition of a 10-m extension tube.

FIG. 5 is a graph showing the respiratory information of the patient after subtraction processing under the condition of a continuous flow of 1 LPM and addition of a 10-m extension tube.

FIG. 6 is a graph showing pressure data including the respiratory information of the patient under the condition of a continuous flow of 3 LPM and addition of a 10-m extension tube.

FIG. 7 is a graph showing PSA pressure recorded beforehand under the condition of a continuous flow of 3 LPM and addition of a 10-m extension tube.

FIG. 8 is a graph showing the respiratory information of the patient after subtraction processing under the condition of a continuous flow of 3 LPM and addition of a 10-m extension tube.

FIG. 9 is a flowchart showing the process concerning embodiment 1.

DESCRIPTION OF EMBODIMENTS

Embodiments of the present invention are explained below with reference to FIGS.

Hardware Configuration of Embodiment 1

Configuration of the PSA type oxygen concentration device concerning the present embodiment is explained using FIG. 1.

PSA type oxygen concentration device 1 is equipped with oxygen generation unit 11 that takes air from the outside of PSA type oxygen concentration device 1, and generates concentrated oxygen gas.

The air taken into oxygen generation unit 11 from the outside of the oxygen device is compressed by compressor 111 and then transferred to cylinder 113 through first switching valve 112. First switching valve 112 makes compressor 111 communicate with any one of multiple cylinders 113 and transfers the compressed air into cylinder 113 while venting other cylinders. Cylinder 113 is filled with an adsorbent adsorbing selectively nitrogen gas. The compressed air passes through cylinder 113 and then decreases its nitrogen gas concentration, and becomes a concentrated oxygen gas. The concentrated oxygen gas is transferred through second switching valve 114 to concentrated oxygen buffer tank 115 and stored there. Second switching valve 114 makes any one of multiple cylinders 113 communicate with or shut off from concentrated oxygen buffer tank 115.

Oxygen generation unit 11 makes compressor 111 communicate with any one of multiple cylinders 113 through first switching valve 112 and, at the same time, makes the cylinder 113, communicating with the compressor 111, communicate with concentrated oxygen buffer tank 115 through second switching valve 114. Thus, compressor 111 communicates with any one of multiple cylinders 113 and concentrated oxygen buffer tank 115, and thus the generated concentrated oxygen gas is supplied to concentrated oxygen buffer tank 115. On the other hand, the cylinder 113 that is not communicating with compressor 111, under the condition of being shut off from concentrated oxygen buffer tank 115 by second switching valve 114, is vented through first switching valve 112. Thus, cylinder 113 is decompressed and the nitrogen gas adsorbed on the adsorbent is released to the outside of the oxygen concentration device.

Normally, the compressed air is transferred to cylinder 113, and then cylinder 113 is shut off from the compressor 111 and vented by first switching valve 112. On the other hand, then vented cylinder 113 is made to communicate with the compressor 111 by first switching valve 112 and proceeds to the process of oxygen compression. Thus, alternate repetition of compression and vent of multiple cylinders 113 by first switching valve 112 enables continuous supply of the concentrated oxygen gas.

An extremely large pressure change in cylinder 113 during the generation of concentrated oxygen causes a periodic pressure fluctuation due to switching between cylinders 113 at the downstream side of cylinders 113 in the oxygen gas flow path. The concentrated oxygen gas stored in concentrated oxygen buffer tank 115 is adjusted by pressure regulating valve 116 so that the pressure fluctuation is attenuated.

The concentrated oxygen gas pressure-regulated in oxygen generation unit 11 is controlled on its flow rate in oxygen flow rate control unit 12 composed of control valve 121 and flowmeter 122, and is supplied through humidifier 101 from oxygen supply port 13 to the outside of the oxygen concentration device. Note that oxygen flow rate control unit 12 may be equipped with either of control valve 121 or flowmeter 122 at the upstream of the flow path, and other configuration may be included in oxygen flow rate control unit 12. Oxygen concentrator 1 can adopt a configuration without humidifier 101.

FIG. 2 schematically illustrates an example of an embodiment of the present invention and is an example of a configuration for acquiring respiratory information of a patient.

Oxygen generated in oxygen concentration device 1 is supplied to a patient through extension tube 2 and nasal cannula 3. Conversely, the patient always breathes also during oxygen inhalation, and a pressure change caused by respiration of the patient is propagated toward nasal cannula 3, extension tube 2 and oxygen concentration device 1.

In the present embodiment, respiratory information acquisition means 4 is connected in the oxygen supply path in order to acquire the respiratory pressure of the patient. FIG. 2 shows, as an example, the case where respiratory information acquisition means 4 is connected to the extension tube. However, respiratory information acquisition means 4 may be connected to any portion between humidifier 101 (oxygen flow rate control unit 12 when oxygen concentration device 1 is not equipped with humidifier 101) and nasal cannula 3. In addition, respiratory information acquisition means 4 may be installed either inside oxygen concentration device 1 or outside oxygen concentration device 1 as a different body from oxygen concentration device 1.

As a result of diligent examination of the inventors of the present application, it has been revealed that, even after the pressure fluctuation is attenuated by pressure regulating valve 116, pressure fluctuation applied to respiratory information acquisition means 4 includes pressure fluctuation caused by compression/decompression during generation of the concentrated oxygen gas. Since the amplitude of the pressure fluctuation during the generation of concentrated oxygen gas is larger than the amplitude of the respiration pressure and the amplitude of the respiration pressure decreases due to a pressure drop caused by the flow passing though the oxygen flow path, it is difficult to determine a respiration pressure waveform of the patient directly from a pressure measured using respiratory information acquisition means 4.

In order to solve this problem, in the present embodiment, respiratory information acquisition means 4 is equipped with orifice 5, fine differential pressure sensor 6 and control unit 7.

One end of fine differential pressure sensor 6 is connected to a branch point arranged on extension tube 2 in the oxygen supply path. That is, at one end of fine differential pressure sensor 6, directly applied is the pressure in the oxygen supply path including both the pressure fluctuation due to compression/decompression during the generation of concentrated oxygen gas and the respiration pressure of the patient. Between fine differential pressure sensor 6 and the branch point in the oxygen supply path, arranged is an atmospheric communication path communicating with atmosphere, and third switching valve 8 is arranged in the atmospheric communication path. Third switching valve 8 is a variable flow rate valve and adjustment of the flow rate enables adjustment of the pressure supplied to fine differential pressure sensor 6.

The other end of fine differential pressure sensor 6 is connected to an oxygen supply path through orifice 5. Since respiratory pressure of patients is usually about ±10-100 Pa, in order to acquire the respiratory pressure using respiratory information acquisition means 4, it is preferable to use a sensor with the range of about ±100 Pa for fine differential pressure sensor 6. When oxygen is supplied from oxygen concentration device, supply pressure is always generated due to the oxygen supply, which is about 300 Pa even at a flow rate of 1 LPM. Thus, when one end of fine differential pressure sensor 6 is connected to the oxygen supply path as mentioned above with the other end of fine differential pressure sensor 6 open to the atmosphere, an over range occurs in fine differential pressure sensor 6. Thus, it is preferable to apply pressure of the gas after passing through orifice 5 to the other end of fine differential pressure sensor 6 to acquire the pressure including the respiratory information of the patient in a range of fine differential pressure sensor 6.

Note that any method can be adopted as long as such a pressure not exceeding the range of fine differential pressure sensor 6 is applied to the other end of fine differential pressure sensor 6 as mentioned above, and the method is not limited to the example of the present embodiment.

Control unit 7 is connected to fine differential pressure sensor 6. Control unit 7 is provided with an input/output interface, a first memory, a second memory and a central processing unit (CPU). Control unit 7 receives and records pressure data, including respiratory information of the patient detected using fine differential pressure sensor 6, and acquires the respiratory information of the patient through the process mentioned below. Note that the first memory and the second memory may be of different components or virtually divided memories in a single component.

On extension tube 2, fourth switching valve 9 is arranged at the downstream side from the branch point in the oxygen supply path. Fourth switching valve is a shut-off valve and allows or shuts the oxygen supply to nasal cannula 3.

Principle of the Process Carried Out in Embodiment 1

The principle of the process carried out in the present embodiment is explained using the data, which were obtained in a device having the configuration show in FIG. 2 by applying the respiratory pressure of a patient respiration model (expiratory pressure: 30 Pa, inspiratory pressure: −50 Pa, BPM: 20 times) from nasal cannula 3, and from which respiratory information was acquired.

A group of data is shown in FIG. 3, FIG. 4, and FIG. 5 that was acquired under the condition of a continuous flow of 1 litter per minute (LPM) and connection of a 10-m extension tube 2 downstream of respiratory information acquisition means 4. A continuous flow is one of the supply methods of the concentrated oxygen gas, and is a method to supply the concentrated oxygen gas continuously at a constant flow rate. FIG. 3 shows the pressure data including the respiratory information of the patient and the PSA pressure data of the oxygen concentration device, and the data for the time span of 0 to about 15 sec after the start of measurement are data for a time span during which the respiratory pressure of the patient is not applied and only the PSA pressure of the oxygen concentration device is measured.

FIG. 4 shows PSA pressure data of the oxygen concentration device that were acquired beforehand and recorded in storage media. Incidentally, the PSA pressure of the oxygen concentration device is a periodic pressure change due to a switching cycle of the adsorption cylinder of the above-mentioned PSA type oxygen concentration device during oxygen generation by the PSA type oxygen concentration device. Thus, the cycle in the waveform of the PSA pressure is the same as the switching cycle of the adsorption cylinders of the oxygen concentration device.

The amplitude of the PSA pressure is about 20 Pa as shown in FIG. 4. In FIG. 3, the respiratory pressure of the patient is superimposed on the PSA pressure, and, under this condition, since the PSA pressure is relatively larger than the respiratory pressure of the patient respiration model, the respiratory pressure of the patient respiration model is buried in the PSA pressure and cannot be observed. Thus, the inventors of the present application repeated diligent examination and, in order to obtain the respiratory pressure of the patient respiration model, devised a method to remove only the PSA pressure component by subtracting the component of FIG. 4 from the component of FIG. 3 using software.

The result of subtraction processing using the software under the condition of the both data in phase is shown in FIG. 5. Incidentally, the subtraction processing is a processing to calculate the difference of both data at an arbitrary time. During the time span of 0 to about 15 sec, as mentioned above, since the oxygen concentration device is in the state of running without applying the respiratory pressure of the patient respiration model, the characteristic waveform is not found. On the other hand, at about 15 sec or later, a periodic pressure fluctuation having an amplitude of about 20 Pa can be observed. That is, the respiratory pressure of the patient respiration model can be detected. Thus, the subtraction processing using software enables acquisition of the respiratory information of the patient even under the conditions where oxygen is inhaled at a continuous flow rate of 1 LPM through a nasal cannula and a 10-m extension tube from the oxygen concentration device.

A group of data is shown in FIG. 6, FIG. 7 and FIG. 8 that was acquired under the condition of a continuous flow of 3 LPM and connection of a 10-m extension tube downstream of the respiratory information acquisition means.

FIG. 6 shows, as in FIG. 3, the pressure data including the respiratory information of the patient and the PSA pressure data of the oxygen concentration device, and the data for the time span of 0 to about 15 sec after the start of measurement are data for a time span during which the respiratory pressure of the patient is not applied and only the PSA pressure of the oxygen concentration device is measured.

FIG. 7 shows the PSA pressure data of the oxygen concentration device that were acquired beforehand and recorded in storage media. A waveform difference between FIG. 7 and FIG. 4 is caused by the actuation cycle for adsorption/desorption of nitrogen by adsorption materials during the concentrated oxygen generation, which differs for each flow rate of the oxygen supply.

As in FIG. 3, also in FIG. 6, the respiratory pressure of the patient respiration model is superimposed on the PSA pressure, and, also under these conditions, since the PSA pressure is relatively larger than the respiratory pressure of the patient respiration model, the respiratory pressure of the patient respiration model is buried in the PSA pressure and cannot be observed. As in FIG. 5, the result of subtraction processing under the condition of the both data in phase is shown in FIG. 8. As in FIG. 5, from about 10 sec after the start of measurement, wherein the respiratory pressure is applied, a periodic pressure fluctuation having an amplitude of about 20 Pa can be observed. That is, the respiratory pressure of the patient respiration model is detected. Thus, in accordance with the above-mentioned method, it is revealed that even under the conditions wherein a 10-m extension tube is added and a flow rate of supply oxygen is set to 3 LPM, respiratory information of the patient can be acquired with good accuracy.

Process Carried Out in Embodiment 1

In step S1, when the electric power supply of oxygen concentration device 1 is turned on, oxygen concentration device 1 starts operation and starts supply of the concentrated oxygen gas. At the same time, control unit 7 receives a measured value of differential pressure sensor 6, the pressure data in the oxygen supply path, and starts recording. In addition, control unit 7 starts counting the time from the start of measurement (when power supply is on) and proceeds to step S2. In this embodiment, control unit 7 acquires the PSA pressure data not including the respiratory information of the patient, corresponding the data shown in FIG. 4 and FIG. 7, from the pressure in the oxygen supply path. Specifically, in step S2, control unit 7 judges whether predetermined time has passed after the start of the measurement of the pressure data in oxygen supply path in step S1. The predetermined time is set at a length allowing acquisition of the pressure data corresponding to at least one cycle of the PSA pressure cycle. Incidentally, a respiratory cycle of a patient has usually a length of about 3 sec and at longest about 6 sec. When a PSA pressure cycle has a length of 6 sec or more, the measured data for one cycle of the PSA pressure contain at least one cycle or more of the respiratory information of the patient. On the other hand, when a PSA pressure cycle has a length of less than 6 sec, since the measured data for one cycle of the PSA pressure does not contain one cycle or longer of the respiratory information of the patient, the predetermined time is preferably 6 sec or more.

Incidentally, control unit 7 can use predetermined values recorded beforehand in a memory of control unit 7 without measuring the PSA pressure data every time the power supply is turned on. However, occurrence of deterioration over time of the adsorption materials with the use of oxygen concentration device 1 decreases the amount of adsorption of nitrogen with deterioration. In that case, nitrogen supposed to be adsorbed will exist as a gas in a cylinder, and thus the gas pressure in the cylinder increases, and, as a result, the PSA pressure is thought to become also higher. Thus, for example, the predetermined value, set before shipment, for the PSA pressure data of the oxygen concentration device causes discrepancy from the actual PSA pressure data after the deterioration over time. Thus, in the subtraction processing in the later step, the discrepancy in the PSA pressure data may work as noise, and lower the accuracy of the calculated respiratory information. Therefore, the PSA pressure data is preferably measured every time the power supply is turned on.

When it is judged that the predetermined time has not elapsed in step S2, control unit 7 goes to step S3, and closes fourth switching valve 9 and opens third switching valve 8. At this time, the degree of opening of third switching valve 8 is preferably set to a predetermined degree of opening that corresponds to a pressure drop caused by both extension tube 2 and nasal cannula 3. The predetermined degree of opening may be selected from multiple predetermined degrees of opening depending on the length of an extension tube. By closing fourth switching valve 9, fine differential pressure sensor 6 is shut off from the portion of the oxygen supply to the patient. Therefore, PSA pressure data not including the respiratory information of the patient can be measured from the pressure in the oxygen supply path.

Subsequently, in step S4, the pressure data in the oxygen supply path are stored in the first memory and the second memory of control unit 7. Incidentally, since data acquisition after the degree of valve opening of a switching valve has stabilized enables obtaining reliable data, data acquisition may start after a certain period (e.g., 0.1 sec) from the beginning of the measurement. After having started the measurement of pressure data concerning the inside of the oxygen supply path, control unit 7 repeats a process of step S3 and step S4 until a predetermined time elapses. That is, for a time span that includes pressure data for at least one cycle of the PSA pressure cycle, PSA pressure data not including the respiratory information of the patient are recorded in the first memory and second memory.

When it is judged that the predetermined time has elapsed in step S2, control unit 7 goes to step S5, and closes third switching valve 8 and fully opens fourth switching valve 9. Accordingly, the oxygen supply to the patient is started. Subsequently, the measured value of fine differential pressure sensor 6 includes the respiratory information of the patient.

Next, in step S6, pressure data concerning the inside of the oxygen supply path are stored in the first memory.

In step S7, prior to the subtraction processing in step S8, phases are confirmed between the data stored in the first memory and the data stored in the second memory, and a phase confirmation processing for matching the both phases is executed if necessary.

The above-mentioned principle of the process carried out in the present embodiment is explained assuming that the data of FIG. 3 and FIG. 4 are in phase. However, the data of FIG. 3 and FIG. 4 may be actually different in their acquisition timing, and, in that case, two data are out of phase. The subtraction processing under an out-of-phase condition outputs the out-of-phase part as noise, and finally accuracy on respiratory information acquisition is lowered. Thus, it is necessary to confirm that both data are in phase for making the subtraction processing on software. Here, the condition under which two data are in phase refers to the condition where time data components indicating the pressure peak (local maxima) of both data measured by control unit 7 are in agreement with each other. Methods to make out-of-phase data in-phase include a method of aligning both data at the PSA pressure peak value, a method of differentiating with time the pressure waveform of both data and aligning the time data components at the point where a temporal change of the measured pressure is large, and the like.

In the present embodiment, at first, control unit 7 takes data for each one cycle of the PSA pressure cycle out of the data stored in the first memory. Specifically, since a time interval between a peak (local maxima) and the next peak of pressure data stored in the first memory is equivalent to one cycle of the PSA pressure cycle, control unit 7 detects each peak of data stored in the first memory, determines a time interval between a peak and the next peak, and takes out data for each time interval of the peak and the next peak. Incidentally, since the data acquired at a certain time after the beginning of the measurement are more reliable as mentioned above, it may be decided not to use the data taken within a certain time after the beginning of the measurement. The same holds for the data stored in the second memory. On the other hand, control unit 7 takes PSA pressure cycle data, which is data for one cycle of the PSA pressure cycle, out of the data stored in the second memory in the same manner as mentioned above.

In step S8, executed is the subtraction processing, wherein the PSA pressure cycle data that are taken out of the data stored in the second memory are subtracted from the data that are processed by phase matching in step S7, taken by each cycle of the PSA pressure cycle, and stored in the first memory. Accordingly, data are obtained that include the respiratory information of the patient for one cycle of the PSA pressure cycle.

Note that, the phase confirmation processing and the subtraction processing are not necessarily executed for the data length of one cycle of the PSA pressure cycle, and alternatively, the data stored in the first memory may be taken out by a predetermined number of cycles of the PSA pressure cycle, and PSA pressure data, that are used for the subtraction processing together with the former data, may be prepared by copying and connecting, for a length of the predetermined number of cycles, the PSA pressure measurement data taken out of the data stored in the second memory.

In step S9, the data acquired in step S8 that include the respiratory information of the patient are analyzed to obtain respiratory information of the patient, such as strength/weakness and a frequency of respiration. In addition, each set of data including the respiratory information of the patient for one cycle of the PSA pressure cycle can be connected together to obtain data including the respiratory information of the patient for the entire period from the power on, which enables acquisition of average respiration strength and a respiratory rate during use time.

In step S10, control unit 7 judges whether the power source of the oxygen concentration device is off or not. When the power supply of the oxygen concentration device is not judged as off in step S10, the flow goes back to step S5, and processes from step S6 to step S9 are repeated.

When the power supply of the oxygen concentration device is judged as off in step S10, the flow chart is terminated.

As mentioned above, in accordance with the present invention, respiratory information of a patient can be acquired from the data of measured respiratory pressure of the patient during the operation of oxygen concentration device by separating a respiration component of the patient from a pressure fluctuation component due to PSA.

REFERENCE SIGNS LIST

1. Oxygen concentration device
11. Oxygen generation unit
12. Oxygen flow rate adjust unit
13. Oxygen supply port
111. Compressor
112. Switching valve
113. Cylinder
114. Switching valve
115. Concentrated oxygen buffer tank
116. Pressure regulating valve
121. Control valve
122. Flowmeter
101. Humidifier
2. Extension tube
3. Nasal cannula
4. Respiratory information acquisition means
5. Orifice
6. Fine differential pressure sensor
7. Control unit
8. Third switching valve
9. Fourth switching valve

The invention claimed is:

1. A respiratory information acquisition device used for a PSA type oxygen concentration device that operates by switching multiple adsorption cylinders, the respiratory information acquisition device comprising:
   a sensor connected to an oxygen supply path of the PSA type oxygen concentration device and configured to measure a first pressure of a periodic pressure fluctuation in the oxygen supply path when oxygen is supplied to a patient from the PSA type oxygen concentration device and a second pressure of a periodic pressure fluctuation in the oxygen supply path when the oxygen is not supplied to the patient from the PSA type oxygen concentration device; and
   a control unit configured to:
      match phases of the first pressure and the second pressure, respectively,
      determine a pressure component to be a pressure signal noise of the PSA type oxygen concentration device based on determining a difference, between the first pressure and the second pressure under the condition where the phases are matched, and on a result of controlling one or more valves of the PSA type oxygen concentration device,
      obtain respiration information of the patient based on the difference between the first pressure and the second pressure, and
      control the PSA type oxygen concentration device based on the respiration information and the determined pressure component of the noise of the PSA type oxygen concentration device.

2. The respiratory information acquisition device according to claim 1, wherein, in the matching of the phases, the control unit is further configured to calculate first data for one cycle of the periodic pressure fluctuation of the first pressure and second data for one cycle of the periodic pressure fluctuation of the second pressure, and match the phases based on the first data and the second data.

3. The respiratory information acquisition device according to claim 1, wherein, in the matching of the phases, the control unit is further configured to detect a peak pressure for each of the first pressure and the second pressure, and match the phases at the peak pressures.

4. The respiratory information acquisition device according to claim 1, wherein the oxygen supply path comprises a switching valve for allowing or shutting a supply of the oxygen from the PSA type oxygen concentration device to the patient.

5. The respiratory information acquisition device according to claim 1, wherein the sensor comprises a fine differential pressure sensor configured to measure a differential pressure between both ends of any point in the oxygen supply path and a point of constant pressure.

6. A respiratory information acquisition method comprising:
   measuring, with a sensor connected to an oxygen supply path of a PSA type oxygen concentration device supplying an oxygen to a patient, a first pressure of a periodic pressure fluctuation in the oxygen supply path when the oxygen is supplied to the patient from the PSA type oxygen concentration device and a second pressure of a periodic pressure fluctuation in the oxygen supply path when the oxygen is not supplied to the patient from the PSA type oxygen concentration device, wherein the PSA type oxygen concentration device operates by switching multiple adsorption cylinders;
   matching, by a processor, phases of the first pressure and the second pressure, respectively;
   determine, by the processor, a pressure component to be a pressure signal noise of the PSA type oxygen concentration device based on determining a difference, between the first pressure and the second pressure under the condition where the phases are matched, and on a result of controlling one or more valves of the PSA type oxygen concentration device;
   obtaining, by the processor, respiration information of the patient based on the difference between the first pressure and the second pressure; and
   controlling the PSA type oxygen concentration device based on the respiration information and the determined pressure component of the noise of the PSA type oxygen concentration device.

7. The respiratory information acquisition device according to claim 1, wherein the control unit is further configured obtain the result of controlling the one or more valves of the PSA type oxygen concentration device in response to turning on the PSA type oxygen concentration device.

* * * * *